US012643839B2

(12) United States Patent
Saluja et al.

(10) Patent No.: US 12,643,839 B2
(45) Date of Patent: Jun. 2, 2026

(54) PROCESS AND A SYSTEM FOR ENHANCING THE YIELD OF LIGHT OLEFINS

(71) Applicant: Indian Oil Corporation Limited, Mumbai (IN)

(72) Inventors: Shikha Saluja, Faridabad (IN); Gadari Saidulu, Faridabad (IN); Madhusudan Sau, Faridabad (IN); Sadhullah Mukthiyar, Faridabad (IN); Terapalli Hari Venkata Devi Prasad, Faridabad (IN); Reshmi Manna, Faridabad (IN)

(73) Assignee: Indian Oil Corporation Limited, Maharashtra (IN)

( * ) Notice: Subject to any disclaimer, the term of this patent is extended or adjusted under 35 U.S.C. 154(b) by 215 days.

(21) Appl. No.: 18/614,527

(22) Filed: Mar. 22, 2024

(65) Prior Publication Data

US 2024/0317657 A1 Sep. 26, 2024

(30) Foreign Application Priority Data

Mar. 24, 2023 (IN) .............................. 202321021238

(51) Int. Cl.
| | |
|---|---|
| C07C 5/333 | (2006.01) |
| B01J 8/38 | (2006.01) |
| B01J 21/12 | (2006.01) |
| B01J 21/20 | (2006.01) |
| B01J 38/38 | (2006.01) |
| C07C 11/04 | (2006.01) |

(52) U.S. Cl.
CPC ............. *C07C 5/3332* (2013.01); *B01J 8/384* (2013.01); *B01J 21/12* (2013.01); *B01J 21/20* (2013.01); *B01J 38/38* (2013.01); *C07C 11/04* (2013.01); *C07C 2521/12* (2013.01)

(58) Field of Classification Search
CPC ... C07C 5/3332; C07C 11/04; C07C 2521/12; C07C 1/24; B01J 8/384; B01J 21/12; B01J 21/20; B01J 38/38; B01J 29/40; B01J 29/90; B01J 38/12; C10G 11/05; C10G 11/182
USPC ......................................................... 585/444
See application file for complete search history.

(56) References Cited

U.S. PATENT DOCUMENTS

| | | | |
|---|---|---|---|
| 4,412,914 A | 11/1983 | Hettinger, Jr. et al. | |
| 4,425,259 A | 1/1984 | Hettinger, Jr. et al. | |
| 4,450,241 A | 5/1984 | Hettinger, Jr. et al. | |
| 5,209,287 A | 5/1993 | Johnson et al. | |
| 5,846,402 A * | 12/1998 | Mandal .................... | B01J 29/80 585/653 |
| 6,585,884 B1 | 7/2003 | Mayes, Jr. | |
| 7,699,975 B2 | 4/2010 | Hedrick | |

(Continued)

*Primary Examiner* — Prem C Singh
*Assistant Examiner* — Francis C Campanell
(74) *Attorney, Agent, or Firm* — BLANK ROME LLP

(57) ABSTRACT

The present disclosure provides a process for high conversion residue cracking in a circulating fluidized bed reactor while integrating it with the dehydration of ethanol. More particularly, the present disclosure relates to an integrated circulating fluidized bed process for the simultaneous dehydration of ethanol and cracking of a hydrocarbon feedstock. By integrating the cracking reactor with ethanol dehydration reactor, more conradson carbon residue feedstock can be processed in cracking reactor while limiting the coke combustor temperature.

14 Claims, 1 Drawing Sheet

(56) References Cited

U.S. PATENT DOCUMENTS

| | | | |
|---|---|---|---|
| 7,767,075 B2 | 8/2010 | Hedrick | |
| 7,867,378 B2 | 1/2011 | Pinho et al. | |
| 7,932,204 B2 | 4/2011 | Towler | |
| 8,273,930 B2 | 9/2012 | Wu et al. | |
| 8,373,013 B2 | 2/2013 | Xie et al. | |
| 8,518,334 B2 | 8/2013 | Towler | |
| 2009/0281363 A1* | 11/2009 | Wu ........................ | C10G 57/00 |
| | | | 585/640 |

* cited by examiner

PROCESS AND A SYSTEM FOR ENHANCING THE YIELD OF LIGHT OLEFINS

RELATED APPLICATION

This application claims priority to Indian Application No. 202321021238, filed Mar. 24, 2023. The contents of this application are hereby incorporated by reference in its entirety.

TECHNICAL FIELD

The present disclosure generally relates to the field of oil and petroleum refining, and in particular to a process and a system for the simultaneous dehydration of ethanol and cracking of a hydrocarbon feedstock for the production of light olefins. The present disclosure is intended to further improve the yield of light olefins.

BACKGROUND OF THE INVENTION

Maximization of light olefins such as ethylene, propylene and butylenes in a fluidized catalytic cracking unit (FCC) requires a higher reaction temperature, a higher catalyst to oil ratio and an appropriate catalyst system. Due to the high demand for light olefins, researchers all over the world are now focused on expanding the ambit of feedstock that can be processed in a catalytic cracking unit. However, the upgradation of residue hydrocarbon feedstock into light olefins has been a challenging task due to higher concentrations of contaminants such as conradson carbon content (CCR) and thereby higher coke deposited on the catalyst. The regenerator (coke combustor) temperature increases with higher coke leading to reduced catalyst circulation or reduced catalyst to oil ratio and thereby decreasing the conversion of hydrocarbon feedstock into light olefins.

To address the above issues, U.S. Pat. No. 5,209,287A discloses the use of a catalyst cooler for the cooling of catalysts in FCC regenerators. U.S. Pat. Nos. 4,412,914, 4,425,259, 4,450,241, 6,585,884, 7,699,975, 7,767,075, 7,932,204, and 8,518,334 disclose the use of a coke gasifier to consume excess heat in order to maintain lower regenerator temperature and to further increase the catalyst to oil ratio. However, the overall production of light olefins is limited due to the significant production of coke and steam in the regenerator.

U.S. Pat. No. 8,273,930B2 discloses a process in which ethanol is converted to ethylene by contacting with a cooled regenerated catalyst in $1^{st}$ reactor. The disadvantage of this process is regenerator is operated at a higher temperature as a large fraction of the spent catalyst from $2^{nd}$ reactor directly enters the regenerator along with the coked catalyst from $1^{st}$ reactor, which would overshoot the regenerator temperature. The higher regenerator temperature will reduce the catalyst to oil ratio and hence reduces conversion. Further, catalyst deactivation increases significantly at higher regenerator temperatures and thereby reduces conversion. Further to this, a hot catalyst from the regenerator is required to be cooled down to 200-450° C. with the help of a direct heat exchanger before entering into the dehydration reactor. The direct heat exchanger deploys low temperature air for contacting with the hot regenerated catalyst, thereby the excess heat is lost in this process. Also, the feed CCR that could be converted in this process is limited. Further, the use of the coked catalyst in $2^{nd}$ reactor reduces the hydrocarbon conversion as well.

U.S. Pat. No. 7,867,378B2 discloses a fluid catalytic cracking process to increase the production of ethylene in which firstly ethanol is dehydrated in the presence of regenerated hot zeolite catalyst in a reactor and output of this reactor containing ethylene product, water as byproduct & unconverted ethanol along with deactivated catalyst is fed into next reactor in which hydrocarbons are fed and cracked to obtain products. This combination results in lower conversion in the main hydrocarbon cracking reactor due to the use of a deactivated catalyst coming from the dehydration reactor. Moreover, the process envisages processing lighter feedstocks.

U.S. Pat. No. 8,373,013B2 discloses a process which combines catalytic conversion of organic oxygenate like ethanol into ethylene and catalytic cracking of hydrocarbons in presence of Y zeolite catalyst. The coked catalyst from the dehydration reactor and spent catalyst from the catalytic cracking reactor are mixed and supplied to the regenerator for decoking and the regenerated catalyst is routed again to the reactors.

Prior art so far describes either the use of a catalyst cooler or the deployment of ethanol dehydration at the upstream of cracking reactor for the removal of excess heat. Deploying ethanol dehydration at the upstream of the cracking reactor would lead to the deactivation of the catalyst, which is entering into the hydrocarbon cracking reactor. Moreover, the temperature of the regenerated catalyst entering into the ethanol dehydration reactor needs to be reduced, as ethanol dehydration is favored at lower temperature i.e., in the range of 350-550° C. Therefore, there is a need for a process which integrate the hydrocarbon residue cracking reactor with dehydration reactor while limiting the regenerator temperature below 700° C. to avoid excessive deactivation and ensuring higher conversion in cracking reactor. In order to address the problems in the art, the present disclosure provides an integration of the endothermic dehydration of ethanol with residue hydrocarbon processing, which results in the utilization of excess heat due to concarbon residue and thereby achieving higher conversion while augmenting light olefins yields in a catalyst cracker unit.

In the present disclosure, the coke-laden catalyst from the hydrocarbon cracking reactor is first sent to the ethanol dehydration reactor for the production of ethylene. The temperature of the coke-laden catalyst in the dehydration reactor reduces due to the endothermic dehydration process. The low temperature catalyst from the dehydration reactor is sent to the coke combustor (regenerator) for coke burning. As the temperature of the incoming deactivated catalyst is lower, the temperature of the coke combustor in the present disclosure will be either lower or at a similar range as compared to that of the prior art with a catalyst cooler. As the coke combustor temperature is lower in the present disclosure, the catalyst to oil ratio increases for the given residue content in the feed, which enhance the conversion of hydrocarbon to light olefins. As a high catalyst to oil ratio is ensured for hydrocarbon cracking, the coke levels on the coke-laden catalyst will be comparatively lower and catalyst will retain sufficient activity for ethanol dehydration reaction. Further, the desired catalyst to oil ratio can be maintained in the present disclosure irrespective of residue content in the feed by varying the ethanol to hydrocarbon ratio. Since, the fully regenerated catalyst is used for hydrocarbon cracking, the yields of light olefins from hydrocarbon will be maximum due to the presence of more active sites on the regenerated catalyst. Moreover, the ethylene yield produced is higher in the present disclosure as the excess heat is completely utilized for the dehydration of ethanol with no additional heat sink like catalyst cooler as compared to the prior art.

SUMMARY OF THE INVENTION

This summary is provided to introduce a selection of concepts in a simplified format that are further described in the detailed description of the invention.

In a first aspect of the present disclosure, there is provided an integrated circulating fluidized bed process for simultaneous dehydration of ethanol and cracking of a hydrocarbon feedstock, wherein the process comprises:

feeding the hydrocarbon feedstock (1) having a conradson carbon content (CCR) of at least 4 wt % and a regenerated catalyst (2) obtained from a coke combustor (a) to a fluidized bed cracking reactor (b);

cracking the hydrocarbon feedstock at a temperature in a range of 490 to 680° C. while depositing coke on the catalyst to obtain a reaction mixture comprising hydrocarbon vapor products and a coke-laden catalyst;

separating the hydrocarbon vapor products and the coke-laden catalyst at the end of the fluidized bed cracking reactor (b), and routing the hydrocarbon vapor products for fractionation (3);

stripping the coke-laden catalyst to remove unseparated hydrocarbon vapor products contained therein;

routing the coke-laden catalyst obtained from the stripping step (4) and ethanol (5) to a dehydration reactor (c) for dehydrating ethanol to ethylene and to obtain a product mixture and a deactivated catalyst, wherein the dehydration reactor (c) is maintained at a temperature in a range of 300 to 600° C., wherein the product mixture (6) is routed to the fluidized bed cracking reactor (b) for fractionation;

routing the deactivated catalyst (7) obtained from the dehydrating step to the coke combustor (a) and burning the coke on the deactivated catalyst in the presence of air or oxygen containing gases (8) at a temperature in a range of 600-700° C. to obtain the regenerated catalyst and flue gas (9); and circulating the regenerated catalyst (2) to the fluidized bed cracking reactor (b) for cracking the hydrocarbon feedstock (1), wherein the process simultaneously increases the cracking of the hydrocarbon feedstock and dehydration of ethanol.

In an embodiment of the present disclosure, there is provided an integrated circulating fluidized bed process for simultaneous dehydration of ethanol and cracking of a hydrocarbon feedstock, wherein the catalyst is a multifunctional micro spherical catalyst.

In an embodiment of the present disclosure, there is provided an integrated circulating fluidized bed process for simultaneous dehydration of ethanol and cracking of a hydrocarbon feedstock, wherein the multifunctional micro spherical catalyst comprises:

1 to 6 wt % of ultra-stable Y zeolite,
8 to 25 wt % of pentasil zeolite which is shape selective,
0 to 8 wt % of active material which is bottom selective,
0 to 1 wt % of rare earth constituents, and
91 to 60 wt % of non-acidic constituents and a binder, wherein the wt % is based on the total weight of the catalyst.

In an embodiment of the present disclosure, there is provided an integrated circulating fluidized bed process for simultaneous dehydration of ethanol and cracking of a hydrocarbon feedstock, wherein the pore size of the ultra-stable Y zeolite is in a range of 8 to 11 Å, wherein the pore size of the shape selective pentasil zeolite is in a range of 5 to 6 Å, and wherein the pore size of the bottom selective active material is in a range of 50 to 1000 Å.

In an embodiment of the present disclosure, there is provided an integrated circulating fluidized bed process for simultaneous dehydration of ethanol and cracking of a hydrocarbon feedstock, wherein the cracking of the hydrocarbon feedstock (1) is carried out at a temperature in a range of 550 to 650° C., a weight hourly space velocity in a range of 40-120 hr$^{-1}$, a catalyst to hydrocarbon ratio is in a range of 3 to 25 (wt/wt), a pressure in a range of 0.9 to 5 Kg/cm$^2$ (g) and a steam to hydrocarbon ratio is in a range of 0.1 to 1.0 wt/wt.

In an embodiment of the present disclosure, there is provided an integrated circulating fluidized bed process for simultaneous dehydration of ethanol and cracking of a hydrocarbon feedstock, wherein the dehydration of the ethanol is carried out at a temperature in a range of 350 to 550° C., a weight hourly space velocity in a range of 1-10 hr$^{-1}$, and a pressure in a range of 0.9 to 5 Kg/cm$^2$ (g).

In an embodiment of the present disclosure, there is provided an integrated circulating fluidized bed process for simultaneous dehydration of ethanol and cracking of a hydrocarbon feedstock, wherein the dehydration reactor (c) is installed downstream of the fluidized bed cracking reactor (b) and upstream of the coke combustor (a).

In an embodiment of the present disclosure, there is provided an integrated circulating fluidized bed process for simultaneous dehydration of ethanol and cracking of a hydrocarbon feedstock, wherein the process does not comprise a separate catalyst cooler or heat exchanger for cooling of the catalyst.

In an embodiment of the present disclosure, there is provided an integrated circulating fluidized bed process for simultaneous dehydration of ethanol and cracking of a hydrocarbon feedstock, wherein the hydrocarbon feedstock with higher CCR can be processed by increasing the ethanol to hydrocarbon ratio while maintaining a desired catalyst to oil ratio.

In an embodiment of the present disclosure, there is provided an integrated circulating fluidized bed process for simultaneous dehydration of ethanol and cracking of a hydrocarbon feedstock, wherein the product mixture from the dehydration reactor (c) comprises ethylene, steam and traces of unconverted ethanol, hydrogen, methane, ethane, propane, and propylene, and wherein ethylene is recovered in a range of 40 to 60 wt % on ethanol basis.

In another aspect of the present disclosure, there is provided an integrated system for simultaneous dehydration of ethanol and cracking of a hydrocarbon feedstock comprising:

a catalytic cracking unit comprising a fluidized bed cracking reactor (b) for receiving the hydrocarbon feedstock (1) and a regenerated catalyst (2), and for cracking the hydrocarbon feedstock to obtain a reaction mixture comprising hydrocarbon products and a coke-laden catalyst;

a dehydration unit comprising a dehydration reactor (c) for receiving the coke-laden catalyst from fluidized bed cracking (b) and ethanol (5), and for dehydrating the ethanol to ethylene and to obtain a product mixture and a deactivated catalyst; and a coke combustor unit comprising a coke combustor (a) for receiving the deactivated catalyst (7) from the dehydration reactor (c), and for regenerating the deactivated catalyst by burning in the presence of air or oxygen containing gases (8).

In an embodiment of the present disclosure, there is provided an integrated system for simultaneous dehydration of ethanol and cracking of a hydrocarbon feedstock, wherein the dehydration reactor (c) is installed downstream of the fluidized bed cracking reactor (b) and upstream of the coke combustor (a).

In an embodiment of the present disclosure, there is provided an integrated system for simultaneous dehydration of ethanol and cracking of a hydrocarbon feedstock, wherein the regenerated catalyst obtained from the coke combustor (a) is circulated to fluidized bed cracking reactor (b).

In an embodiment of the present disclosure, there is provided an integrated system for simultaneous dehydration of ethanol and cracking of a hydrocarbon feedstock, wherein the integrated system does not include a separate catalyst cooling unit for cooling of the coke-laden catalyst.

In an embodiment of the present disclosure, there is provided an integrated system for simultaneous dehydration of ethanol and cracking of a hydrocarbon feedstock, wherein the fluidized bed cracking reactor (b) is a circulating fluidized cracking reactor.

In an embodiment of the present disclosure, there is provided an integrated system for simultaneous dehydration of ethanol and cracking of a hydrocarbon feedstock, wherein the fluidized bed cracking reactor (b) is operated at a temperature in a range of 490 to 680° C., a weight hourly space velocity in a range of 40-120 $hr^{-1}$, and a pressure in a range of 0.9 to 5 $Kg/cm^2$ (g).

In an embodiment of the present disclosure, there is provided an integrated system for simultaneous dehydration of ethanol and cracking of a hydrocarbon feedstock, wherein the dehydration reactor (c) is operated at a temperature in a range of 300 to 600° C., a weight hourly space velocity in a range of 1-10 $hr^{-1}$, and a pressure in a range of 0.9 to 5 $Kg/cm^2$ (g).

These and other features, aspects, and advantages of the present invention will become better understood with reference to the following description and appended claims. This summary is provided to introduce a selection of concepts in a simplified form. This summary is not intended to identify key features or essential features of the claimed subject matter, nor is it intended to be used to limit the scope of the claimed subject matter.

BRIEF DESCRIPTION OF ACCOMPANYING DRAWINGS

The following drawings form part of the present specification and are included to further demonstrate certain aspects of the present disclosure, the inventions of which can be better understood by reference to one or more of these drawings in combination with the detailed description of specific embodiments presented herein.

Figure 1:
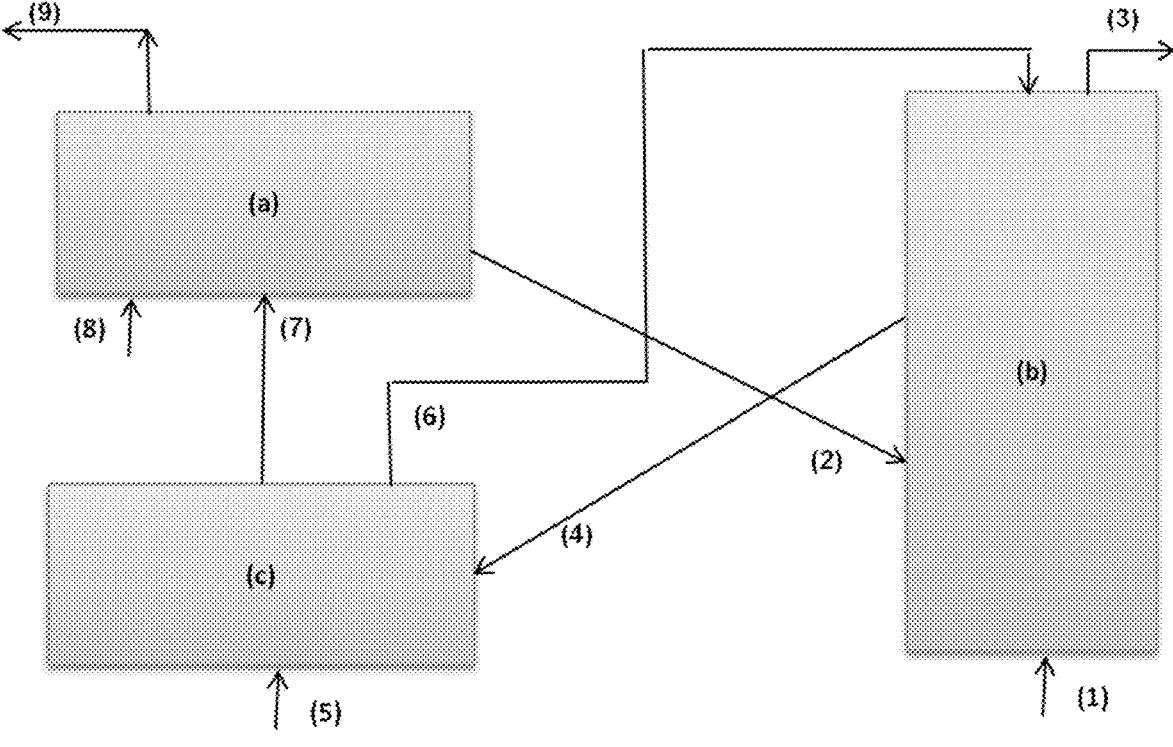
FIG. 1 illustrates a schematic flow diagram of the catalytic cracking unit, according to an embodiment of the present disclosure. The components include fluid bed cracking reactor (b), coke combustor (a), hydrocarbon feedstock (1), dehydration reactor (c), and ethanol (5).

Further, the skilled in the art will appreciate that elements in the drawings are illustrated for simplicity and may not have necessarily been drawn to scale.

DETAILED DESCRIPTION OF THE INVENTION

Those skilled in the art will be aware that the present disclosure is subject to variations and modifications other than those specifically described. It is to be understood that the present disclosure includes all such variations and modifications. The disclosure also includes all such steps of the process, features of the invention, referred to or indicated in this specification, individually or collectively, and any and all combinations of any or more of such steps or features.

Definitions: For convenience, before further description of the present disclosure, certain terms employed in the specification, and examples are collected here. These definitions should be read in the light of the remainder of the disclosure and understood as by a person skilled in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article. The terms "comprise" and "comprising" are used in the inclusive, open sense, meaning that additional elements may be included. It is not intended to be construed as "consists of only". Throughout this specification, unless the context requires otherwise the word "comprise", and variations such as "comprises" and "comprising", will be understood to imply the inclusion of a stated element or step or group of elements or steps but not the exclusion of any other element or step or group of elements or steps.

As used in this disclosure, a "hydrocarbon feedstock" refers to heavy oils left-over from petroleum distillation that can be further refined in a catalytic cracking unit. Examples of hydrocarbon feedstock are vacuum gas oil, coker gas oil, deasphalted oil, hydrogenated bottom, atmospheric residuum, vacuum residuum, and mixtures thereof.

As used in this disclosure, a "feed conradson carbon content (CCR)" refers to carbonaceous residue formed after thermal destruction of hydrocarbon. It is a direct indication of coke forming tendency of the hydrocarbon feedstock.

As used in this disclosure, "light olefins" refer to designate C2 to C4 olefins, e.g., ethylene, propylene, and butylenes.

As used in this disclosure, a "catalyst" refers to any substance which increases the rate of a specific chemical reaction. Catalysts described in this disclosure may be utilized to promote various reactions, such as, but not limited to, cracking (including aromatic cracking), demetalization, desulfurization, and denitrogenation. As used in this disclosure, "cracking" generally refers to a chemical reaction where a molecule having carbon to carbon bonds is broken into more than one molecule by the breaking of one or more of the carbon to carbon bonds, or is converted from a compound which includes a cyclic moiety, such as a cycloalkane, cycloalkane, naphthalene, an aromatic or the like, to a compound which does not include a cyclic moiety or contains fewer cyclic moieties than prior to cracking.

As used in this disclosure, a "regenerated catalyst" refers to a catalyst that has been introduced to a cracking reaction zone and then regenerated in a regenerator (coke combustor) to remove at least a portion of the coke from the catalyst to restore at least a portion of the catalytic activity of the catalyst, or both.

As used in this disclosure, a "multifuctional catalyst" refers to a catalyst that is capable of catalyze both cracking as well as dehydration reaction.

As used in this disclosure, a "coke-laden catalyst" refers to a catalyst that has been introduced to and passed through a cracking reaction zone to crack a hydrocarbon material, resulting in deposition of coke on its surface, and has not been regenerated in the coke combustor following introduction to the cracking reaction zone.

As used in this disclosure, a "deactivated catalyst" refers to a catalyst that has been introduced to and passed through a dehydration reaction zone, resulting in further deposition of coke on its surface, and has not been regenerated in the coke combustor, therefore resulting in the temporary deactivation of catalyst. As used in this disclosure, a "reactor" refers to a vessel in which one or more chemical reactions may occur between one or more reactants optionally in the presence of one or more catalysts.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the disclosure, the preferred methods, and materials are now described. All publications mentioned herein are incorporated herein by reference. The present disclosure is not to be limited in scope by the specific embodiments described herein, which are intended for the purposes of exemplification only. Functionally equivalent products and methods are clearly within the scope of the disclosure, as described herein.

In a first aspect of the present disclosure, there is provided an integrated circulating fluidized bed process for simultaneous dehydration of ethanol and cracking of a hydrocarbon feedstock, wherein the process comprises:

feeding the hydrocarbon feedstock (1) having a conradson carbon content (CCR) of at least 4 wt % and a regenerated catalyst (2) obtained from a coke combustor (a) to a fluidized bed cracking reactor (b);

cracking the hydrocarbon feedstock at a temperature in a range of 490 to 680° C. while depositing coke on the catalyst to obtain a reaction mixture comprising hydrocarbon vapor products and a coke-laden catalyst;

separating the hydrocarbon vapor products and the coke-laden catalyst at the end of the fluidized bed cracking reactor (b), and routing the hydrocarbon vapor products for fractionation (3);

stripping the coke-laden catalyst to remove unseparated hydrocarbon vapor products contained therein;

routing the coke-laden catalyst obtained from the stripping step (4) and ethanol (5) to a dehydration reactor (c) for dehydrating ethanol to ethylene and to obtain a product mixture and a deactivated catalyst, wherein the dehydration reactor (c) is maintained at a temperature in a range of 300 to 600° C., wherein the product mixture (6) is routed to the fluidized bed cracking reactor (b) for fractionation;

routing the deactivated catalyst (7) obtained from the dehydrating step to the coke combustor (a) and burning the coke on the deactivated catalyst in the presence of air or oxygen containing gases (8) at a temperature in a range of 600-700° C. to obtain the regenerated catalyst and flue gas (9); and circulating the regenerated catalyst (2) to the fluidized bed cracking reactor (b) for cracking the hydrocarbon feedstock (1), wherein the process simultaneously increases the cracking of the hydrocarbon feedstock and dehydration of ethanol.

In an embodiment of the present disclosure, there is provided an integrated circulating fluidized bed process for simultaneous dehydration of ethanol and cracking of a hydrocarbon feedstock, wherein the hydrocarbon feedstock is selected from the group consisting of vacuum gas oil, coker gas oil, deasphalted oil, hydrogenated bottom, atmospheric residuum, vacuum residuum, and mixtures thereof.

In an embodiment of the present disclosure, there is provided an integrated circulating fluidized bed process for simultaneous dehydration of ethanol and cracking of a hydrocarbon feedstock, wherein the hydrocarbon vapor products obtained from the cracking step comprises of propylene, ethylene, butylenes, hydrogen, ethane, ethane, propane, butane, isobutene, light cracked naphtha, heavy cracked naphtha, light cycle oil, heavy cycle oil, clarified oil etc.

In an embodiment of the present disclosure, there is provided an integrated circulating fluidized bed process for simultaneous dehydration of ethanol and cracking of a hydrocarbon feedstock, wherein the product mixture obtained from the dehydration reactor (c) is routed downstream of the fluidized bed cracking reactor (b) for fractionation to obtain a light olefin fraction, wherein the light olefin fraction comprises of mainly ethylene obtained by dehydration of ethanol and hydrocarbon cracking, and C3-C4 olefins obtained from hydrocarbon cracking.

In an embodiment of the present disclosure, there is provided an integrated circulating fluidized bed process for simultaneous dehydration of ethanol and cracking of a hydrocarbon feedstock, wherein the catalyst is a multifunctional micro spherical catalyst.

In an embodiment of the present disclosure, there is provided an integrated circulating fluidized bed process for simultaneous dehydration of ethanol and cracking of a hydrocarbon feedstock, wherein the multifunctional micro spherical catalyst comprises:

1 to 6 wt % of ultra-stable Y zeolite, 8 to 25 wt % of pentasil zeolite which is shape selective, 0 to 8 wt % of active material which is bottom selective, 0 to 1 wt % of rare earth constituents, and 91 to 60 wt % of non-acidic constituents and a binder, wherein the wt % is based on the total weight of the catalyst.

In an embodiment of the present disclosure, there is provided an integrated circulating fluidized bed process for simultaneous dehydration of ethanol and cracking of a hydrocarbon feedstock, wherein the bottom selective active material is alumina or peptized alumina.

In an embodiment of the present disclosure, there is provided an integrated circulating fluidized bed process for simultaneous dehydration of ethanol and cracking of a hydrocarbon feedstock, wherein the rare earth constituents include oxides of lanthanum or cerium.

In an embodiment of the present disclosure, there is provided an integrated circulating fluidized bed process for simultaneous dehydration of ethanol and cracking of a hydrocarbon feedstock, wherein the non-acidic constituents include silica, alumina, or natural clay like kaolin, kaolinite etc.

In an embodiment of the present disclosure, there is provided an integrated circulating fluidized bed process for simultaneous dehydration of ethanol and cracking of a hydrocarbon feedstock, wherein the pore size of the ultra-stable Y zeolite is in a range of 8 to 11 Å, wherein the pore size of the shape selective pentasil zeolite is in a range of 5 to 6 Å, and wherein the pore size of the bottom selective active material is in a range of 50 to 1000 Å.

In an embodiment of the present disclosure, there is provided an integrated circulating fluidized bed process for simultaneous dehydration of ethanol and cracking of a hydrocarbon feedstock, wherein the cracking of the hydrocarbon feedstock (1) is carried out at a temperature in a range of 550 to 650° C., a weight hourly space velocity in a range of 40-120 hr$^{-1}$, a catalyst to hydrocarbon ratio is in a range of 3 to 25 (wt/wt), a pressure in a range of 0.9 to 5 Kg/cm$^2$ (g) and a steam to hydrocarbon ratio is in a range of 0.1 to 1.0 wt/wt.

In an embodiment of the present disclosure, there is provided an integrated circulating fluidized bed process for simultaneous dehydration of ethanol and cracking of a hydrocarbon feedstock, wherein the dehydration of the ethanol is carried out at a temperature in a range of 350 to 550° C., a weight hourly space velocity in a range of 1-10 hr$^{-1}$, and a pressure in a range of 0.9 to 5 Kg/cm$^2$ (g).

In an embodiment of the present disclosure, there is provided an integrated circulating fluidized bed process for simultaneous dehydration of ethanol and cracking of a hydrocarbon feedstock, wherein the dehydration reactor (c) is installed downstream of the fluidized bed cracking reactor (b) and upstream of the coke combustor (a).

In an embodiment of the present disclosure, there is provided an integrated circulating fluidized bed process for simultaneous dehydration of ethanol and cracking of a hydrocarbon feedstock, wherein the process does not comprise a separate catalyst cooler or heat exchanger for cooling of the catalyst.

In an embodiment of the present disclosure, there is provided an integrated circulating fluidized bed process for simultaneous dehydration of ethanol and cracking of a hydrocarbon feedstock, wherein the hydrocarbon feedstock with higher CCR can be processed by increasing the ethanol to hydrocarbon ratio while maintaining a desired catalyst to oil ratio.

In an embodiment of the present disclosure, there is provided an integrated circulating fluidized bed process for simultaneous dehydration of ethanol and cracking of a hydrocarbon feedstock, wherein the desired catalyst to oil ratio is in a range of 5-20.

In an embodiment of the present disclosure, there is provided an integrated circulating fluidized bed process for simultaneous dehydration of ethanol and cracking of a hydrocarbon feedstock, wherein the ethanol to hydrocarbon ratio is in a range of 0-2 wt/wt.

In an embodiment of the present disclosure, there is provided an integrated circulating fluidized bed process for simultaneous dehydration of ethanol and cracking of a hydrocarbon feedstock, wherein the product mixture comprises ethylene, steam and traces of unconverted ethanol, hydrogen, methane, ethane, propane, and propylene, and wherein ethylene is recovered in a range of 40 to 60 wt % on ethanol basis.

In another aspect of the present disclosure, there is provided an integrated system for simultaneous dehydration of ethanol and cracking of a hydrocarbon feedstock comprising:

a catalytic cracking unit comprising a fluidized bed cracking reactor (b) for receiving the hydrocarbon feedstock (1) and a regenerated catalyst (2), and for cracking the hydrocarbon feedstock to obtain a reaction mixture comprising hydrocarbon products and a coke-laden catalyst;

a dehydration unit comprising a dehydration reactor (c) for receiving the coke-laden catalyst from fluidized bed cracking (b) and ethanol (5), and for dehydrating the ethanol to ethylene and to obtain a product mixture and a deactivated catalyst; and a coke combustor unit comprising a coke combustor (a) for receiving the deactivated catalyst (7) from the dehydration reactor (c), and for regenerating the deactivated catalyst by burning in the presence of air or oxygen containing gases (8).

In an embodiment of the present disclosure, there is provided an integrated system for simultaneous dehydration of ethanol and cracking of a hydrocarbon feedstock, wherein the dehydration reactor (c) is installed downstream of the fluidized bed cracking reactor (b) and upstream of the coke combustor (a).

In an embodiment of the present disclosure, there is provided an integrated system for simultaneous dehydration of ethanol and cracking of a hydrocarbon feedstock, wherein the regenerated catalyst obtained from the coke combustor (a) is circulated to fluidized bed cracking reactor (b).

In an embodiment of the present disclosure, there is provided an integrated system for simultaneous dehydration of ethanol and cracking of a hydrocarbon feedstock, wherein the integrated system does not include a separate catalyst cooling unit for cooling of the catalyst.

In an embodiment of the present disclosure, there is provided an integrated system for simultaneous dehydration of ethanol and cracking of a hydrocarbon feedstock, wherein the fluidized bed cracking reactor (a) is a circulating fluidized cracking reactor.

In an embodiment of the present disclosure, there is provided an integrated system for simultaneous dehydration of ethanol and cracking of a hydrocarbon feedstock, wherein the fluidized bed cracking reactor (b) is operated at a temperature in a range of 490 to 680° C., a weight hourly space velocity in a range of 40-120 hr$^{-1}$, and a pressure in a range of 0.9 to 5 Kg/cm$^2$ (g).

In an embodiment of the present disclosure, there is provided an integrated system for simultaneous dehydration of ethanol and cracking of a hydrocarbon feedstock, wherein the dehydration reactor (c) is operated at a temperature in a range of 300 to 600° C., a weight hourly space velocity in a range of 1-10 hr$^{-1}$, and a pressure in a range of 0.9 to 5 Kg/cm$^2$ (g).

The following description describes the process and the system in detail, according to the present disclosure.

FIG. 1 illustrates the catalytic cracking unit comprising of a fluid bed cracking reactor (1) for processing a heavier hydrocarbon feedstock (1) having CCR of at least 4 wt %. The regenerated catalyst (2) from the coke combustor at a temperature in a range of 600-700° C. enters into the fluid bed cracking reactor (b), wherein it comes in contact with the hydrocarbon feedstock (1). The hydrocarbon feed gets vaporized instantaneously and get cracked in the presence of the catalyst in the fluid bed cracking reactor (b). The reactor outlet temperature is maintained in a range of 550 to 650° C. by adjusting a catalyst to oil ratio. During the cracking, the catalyst gets deactivated with the deposition of coke and other feed impurities. The separation of the coke-laden catalyst and hydrocarbon product vapors is carried at the end of the fluid bed cracking reactor (b). The coke-laden catalyst is sent to a dehydration reactor (c) after stripping off the hydrocarbons (unseparated hydrocarbon vapor products). Ethanol (5) is introduced into the dehydration reactor, where ethanol is dehydrated to ethylene in the presence of the coke-laden catalyst. The temperature of the ethanol dehydration reactor is maintained in a range of 350 to 550° C. depending on the CCR of the hydrocarbon feed. Since the dehydration reaction is highly endothermic, there is no requirement for a catalyst cooler to reduce the catalyst temperature. As the feed CCR increases, the dehydration reactor temperature is to be reduced by increasing ethanol to hydrocarbon ratio so that coke combustor temperature is maintained below 700° C. The dehydration reactor product mixture comprising ethylene, steam and traces of hydrocarbon like hydrogen, methane, ethane, propane, propylene is routed downstream of the fluid bed cracking reactor (b) for fractionation. The product mixture from dehydration reactor contains 40-60 wt % of ethylene. In addition to coke deposition during cracking, 0.1 to 0.25 wt % coke is also deposited on the catalyst during the dehydration of ethanol.

The deactivated catalyst from the dehydration reactor is then sent to a coke combustor (a), where coke deposited on the catalyst is burnt with air or oxygen containing gases at a temperature in a range of 600-700° C., and the activity of the catalyst is regained. After coke burning, the regenerated catalyst is circulated to the fluid bed cracking reactor (b).

The following description describes the conditions employed in the process or system, and the catalyst, according to the present disclosure.

The residue hydrocarbon feedstock having CCR of at least 4 wt % is cracked in a reactor in the presence of a multifunctional micro spherical catalyst consisting of 1 to 6 wt % of ultra-stable Y-zeolite; from 8 to 25 wt % of pentasil zeolite which is shape selective; from 0 to 8 wt % of active material which is bottom selective; from 0 to 1 wt % of rare earth constituents; and from 91 to 60 wt % of non-acidic constituents and a binder. The pore size of USY-zeolite is in a range of 8-11 Å; shape selective pentasil zeolite in a range of 5-6 Å; and bottom selective active material in a range of 50-1000 Å. The cracking of hydrocarbons is carried out in the operating temperature ranging from 490 to 680° C., preferably between 550° C. to 650° C. and desired operating pressure ranging from 0.9 to 5 Kg/cm$^2$ (g), preferably between 1.0 to 1.5 Kg/cm$^2$ (g). The weight hourly space velocity (WHSV) is maintained in a range of 40-120 hr$^{-1}$, and the ratio of the catalyst to hydrocarbons may be kept between 3 to 25 (wt/wt), preferably between 5 to 22. The residence time provided in the cracking reactor is kept in the range of 1 to 10 seconds, preferably between 3 to 7 seconds. The dehydration reactor operated at a pressure ranging from 0.9 to 5 kg/cm$^2$ (g) and weight hourly space velocity (WHSV) of 1-10 hr$^{-1}$. The temperature of the ethanol dehydration reactor is maintained in a range of 300 to 600° C., preferably between 350° C. to 550° C. The resultant reaction mixture shall consist of cracked hydrocarbons having total ethylene yield in a range of 40-60 wt %. The other gaseous products produced by cracking and dehydration processes are propylene, butylenes, methane, hydrogen, propane, butane etc. The liquid product produced in the process can be fractionated as per the desired cut range. The catalyst gets deactivated during the cracking step due to deposition of coke. The coke consists of carbon, hydrogen, sulfur, nitrogen and metals (Ni, Na, V, Fe and other trace metals present in the feedstock).

Although the subject matter has been described in considerable detail with reference to certain preferred embodiments thereof, other embodiments are possible.

EXAMPLES

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods, the exemplary methods, devices and materials are described herein. It is to be understood that this disclosure is not limited to particular methods, and experimental conditions described, as such methods and conditions may vary. Person skilled in the art will be aware of the fact that the present examples will further subject to variations and modifications specifically described herein based on the technical requirement of the experiment and shall not be limiting what specifically mentioned.

Materials and Process

The catalytic cracking experiments were carried out in a fixed bed microreactor unit, using coke-laden catalyst obtained from a commercial high severity fluid catalytic cracking unit. The coke on the catalyst was 0.65%. Analytical grade ethanol (purity—99.99%) was used in the experiments. The commercial operating conditions estimated for dehydration reactor was maintained by keeping WHSV: 5 hr$^{-1}$. Ethanol feed was contacted with the catalyst bed to obtain a reaction mixture at the downstream of the reactor. The product gas from the reactor was passed through a chiller where liquid fraction was separated from the gas phase, and the liquid and gas samples obtained were analyzed using Gas chromatography methods. The deactivated catalyst was then regenerated by passing air through the catalyst bed. The experiment was repeated with regenerated catalyst to evaluate the effect of 'coke on catalyst' on the dehydration reaction.

Example 1

The experimental data for dehydration of ethanol has been generated using a commercial coke-laden catalyst (with 0.65% coke on spent catalyst) as well as a regenerated catalyst in order to study the effect of deactivation of catalyst on the ethylene yield obtained by dehydration of ethanol.

TABLE 1

Describe the effect of the deactivation of catalyst on dehydration of ethanol.

|  |  | Coke-laden catalyst | Regenerated catalyst |
|---|---|---|---|
| Temperature | ° C. | 400 | 400 |
| WHSV | hr−1 | 5 | 5 |
| Butylenes | wt % | 0.5 | 0.5 |
| Propylene | wt % | 0.31 | 0.33 |
| Ethylene | wt % | 55.78 | 56.05 |

The data provided in Table 1 indicates that, there is no noticeable loss in ethylene yield at 400° C. with the coke-laden catalyst as compared to the regenerated catalyst.

Example 2

The effect of an increase in temperature on ethanol dehydration has been illustrated in Table 2. It has been validated that beyond 400° C. with an increase in temperature, ethylene yield decreases and therefore the limitation note for prior art U.S. Pat. No. 7,867,378 is being addressed in the present disclosure.

TABLE 2

Describe the effect of temperature on ethylene yield obtained from dehydration of ethanol using regenerated catalyst.

| | | Temperature | | | | | | |
|---|---|---|---|---|---|---|---|---|
| °C. | | 300 | 350 | 400 | 450 | 500 | 550 | 600 |
| WHSV | hr-1 | 5 | 5 | 5 | 5 | 5 | 5 | 5 |
| Butylenes | wt % | 1.2 | 0.5 | 0.5 | 0.6 | 2.2 | 1.1 | 1.1 |
| Propylene | wt % | 0.68 | 0.31 | 0.33 | 0.43 | 1.66 | 1.71 | 2.35 |
| Ethylene | wt % | 5.56 | 31.93 | 56.05 | 54.39 | 52.57 | 51.73 | 47.83 |

Example 3

Figure 2:
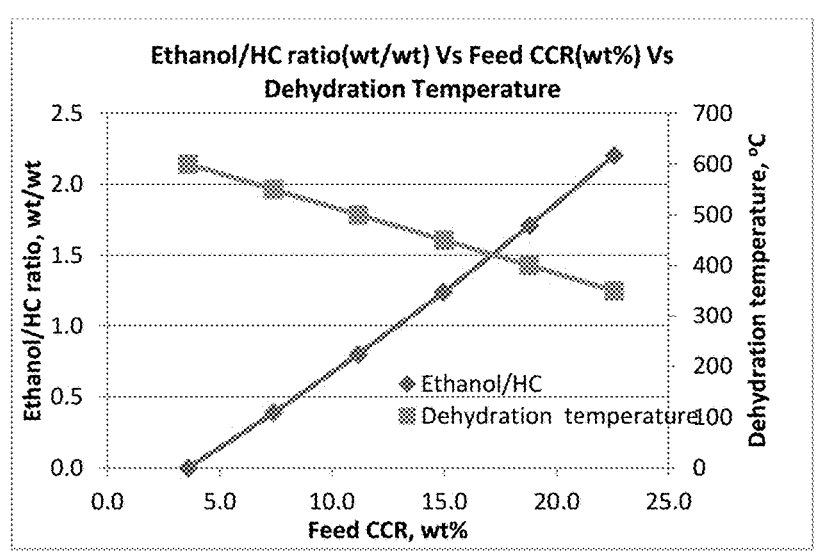
FIG. 2 illustrates the variations in the ethanol to hydrocarbon ratio and dehydration temperature with the feed CCR.

In order to estimate the ethanol to hydrocarbon ratio required for a given feed CCR and the corresponding dehydration temperature, heat balance calculations of the system were worked out for a cracking temperature of 600° C. and coke combustor temperature of 700° C. The variation in the ethanol to hydrocarbon ratio and dehydration temperature with feed CCR has been illustrated in FIG. 2.

It is observed that the ethanol to hydrocarbon ratio increases with an increase in the feed CCR while the dehydration temperature decreases in order to control the temperature of the combustor. This indicates that the present disclosure provides flexibility for the feed CCR that can be processed in the cracking reactor by varying the ethanol to hydrocarbon ratio.

Overall, the present disclosure provides an integrated circulating fluidized bed process and a system for the simultaneous dehydration of ethanol and cracking of a hydrocarbon feedstock. The present disclosure provides a higher conversion of residue hydrocarbon while maintaining the desired catalyst to oil independent of feed heaviness. It results in a high yield of light olefins due to the conversion of ethanol to ethylene in the dehydrator reactor. The present disclosure expands the ambit of feedstock that can be processed in the catalytic cracking process. The present disclosure prevents the catalyst from thermal deactivation by maintaining a lower coke combustor temperature due to the integration of the endothermic dehydration of ethanol.

It will thus be seen that the objects set forth above, among those made apparent from the preceding description, are efficiently attained, and since certain changes may be made in the constructions set forth without departing from the spirit and scope of the invention, it is intended that all matter contained in the above description shall be interpreted as illustrative and not in a limiting sense. The invention has been described with reference to preferred and alternate embodiments. Modifications and alterations will become apparent to those skilled in the art upon reading and understanding the detailed discussion of the invention provided herein. This invention is intended to include all such modifications and alterations insofar as they come within the scope of the present invention. These and other modifications of the preferred embodiments as well as other embodiments of the invention will be obvious from the disclosure herein, whereby the foregoing descriptive matter is to be interpreted merely as illustrative of the invention and not as a limitation.

Finally, to the extent necessary to understand or complete the disclosure of the present invention, all publications, patents, and patent applications mentioned herein are expressly incorporated by reference therein to the same extent as though each were individually so incorporated.

We claim:

1. An integrated circulating fluidized bed process for simultaneous dehydration of ethanol and cracking of a hydrocarbon feedstock, wherein the process comprises:
   feeding the hydrocarbon feedstock having a conradson carbon content (CCR) of at least 4 wt % and a regenerated catalyst obtained from a coke combustor to a fluidized bed cracking reactor;
   cracking the hydrocarbon feedstock at a temperature in a range of 490 to 680° C. while depositing coke on the regenerated catalyst to obtain a reaction mixture comprising hydrocarbon vapor products and a coke-laden catalyst;
   separating the hydrocarbon vapor products and the coke-laden catalyst at the end of the fluidized bed cracking reactor, and routing the hydrocarbon vapor products for fractionation;
   stripping the coke-laden catalyst to remove unseparated hydrocarbon vapor products contained therein;
   routing the coke-laden catalyst obtained from the stripping step and ethanol to a dehydration reactor for dehydrating ethanol to ethylene and to obtain a product mixture and a deactivated catalyst, wherein the dehydration reactor is maintained at a temperature in a range of 300 to 600° C., wherein the product mixture is routed to the fluidized bed cracking reactor for fractionation;
   routing the deactivated catalyst obtained from the dehydrating step to the coke combustor and burning the coke on the deactivated catalyst in the presence of air or oxygen containing gases at a temperature in a range of 600-700° C. to obtain the regenerated catalyst and flue gas; and
   circulating the regenerated catalyst to the fluidized bed cracking reactor for cracking the hydrocarbon feedstock,
   wherein the process is carried out without a separate catalyst cooler or a heat exchanger, and wherein the dehydration of ethanol yields ethylene in a range of 40 to 60 wt % on ethanol basis.

2. The process as claimed in claim 1, wherein the catalyst is a multifunctional micro spherical catalyst.

3. The process as claimed in claim 2, wherein the multifunctional micro spherical catalyst comprises:
   1 to 6 wt % of ultra-stable Y zeolite;
   8 to 25 wt % of shape selective pentasil zeolite;
   0 to 8 wt % of bottom selective active material;
   0 to 1 wt % of rare earth constituents; and
   91 to 60 wt % of non-acidic constituents and a binder,
   wherein the wt % is based on the total weight of the multifunctional micro spherical catalyst.

4. The process as claimed in claim 3, wherein the pore size of the ultra-stable Y zeolite is in a range of 8 to 11 Å, wherein the pore size of the shape selective pentasil zeolite is in a range of 5 to 6 Å, and wherein the pore size of the bottom selective active material is in a range of 50 to 1000 Å.

5. The process as claimed in claim 1, wherein the cracking of the hydrocarbon feedstock is carried out at a temperature in a range of 550 to 650° C., a weight hourly space velocity in a range of 40 to 120 hr$^{-1}$, a catalyst to hydrocarbon ratio is in a range of 3 to 25 (wt/wt), a pressure in a range of 0.9 to 5 Kg/cm$^2$ (g) and a steam to hydrocarbon ratio is in a range of 0.1 to 1.0 wt/wt.

6. The process as claimed in claim 1, wherein the dehydration of the ethanol is carried out at a temperature in a range of 350 to 550° C., a weight hourly space velocity in a range of 1 to 10 hr$^{-1}$, and a pressure in a range of 0.9 to 5 Kg/cm$^2$ (g).

7. The process as claimed in claim 1, wherein the dehydration reactor is installed downstream of the fluidized bed cracking reactor and upstream of the coke combustor.

8. The process as claimed in claim 1, wherein the product mixture comprises ethylene, steam and traces of unconverted ethanol, hydrogen, methane, ethane, propane, and propylene.

9. An integrated system for simultaneous dehydration of ethanol and cracking of a hydrocarbon feedstock comprising:

a catalytic cracking unit comprising a fluidized bed cracking reactor operated at a temperature in a range of 490 to 680° C. for receiving the hydrocarbon feedstock and a regenerated catalyst, and for cracking the hydrocarbon feedstock to obtain a reaction mixture comprising hydrocarbon products and a coke-laden catalyst;

a dehydration unit comprising a dehydration reactor operated at a temperature in a range of 300 to 600° C. for receiving the coke-laden catalyst from fluidized bed cracking and ethanol, and for dehydrating the ethanol to ethylene and to obtain a product mixture and a deactivated catalyst, wherein the dehydration of ethanol yields ethylene in a range of 40 to 60 wt % on ethanol basis; and a coke combustor unit comprising a coke combustor for receiving the deactivated catalyst from the dehydration reactor, and for regenerating the deactivated catalyst by burning in the presence of air or oxygen containing gases, wherein the integrated system excludes a separate catalyst cooler or a heat exchanger.

10. The integrated system as claimed in claim 9, wherein the dehydration reactor is installed downstream of the fluidized bed cracking reactor and upstream of the coke combustor.

11. The integrated system as claimed in claim 9, wherein the regenerated catalyst obtained from the coke combustor is circulated to the fluidized bed cracking reactor.

12. The integrated system as claimed in claim 9, wherein the fluidized bed cracking reactor is a circulating fluidized cracking reactor.

13. The integrated system as claimed in claim 9, wherein the fluidized bed cracking reactor is operated at a weight hourly space velocity in a range of 40 to 120 $hr^{-1}$, and a pressure in a range of 0.9 to 5 $Kg/cm^2$ (g).

14. The integrated system as claimed in claim 9, wherein the dehydration reactor is operated at a weight hourly space velocity in a range of 1 to 10 $hr^{-1}$, and a pressure in a range of 0.9 to 5 $Kg/cm^2$ (g).

* * * * *